United States Patent [19]

Barbier

[11] Patent Number: 5,072,595

[45] Date of Patent: Dec. 17, 1991

[54] APPARATUS FOR DETECTING SMALL BUBBLES IN A PRESSURIZED FLUID STREAM

[76] Inventor: William J. Barbier, 6720 Christina Marie La., Hazelwood, Mo. 63042

[21] Appl. No.: 584,696

[22] Filed: Sep. 19, 1990

[51] Int. Cl.⁵ .............................. G01N 53/00
[52] U.S. Cl. ........................ 62/129; 62/152; 250/577; 340/619; 73/19.01
[58] Field of Search .............. 62/129, 125, 126, 127, 62/151, 152, 196.4, 278; 340/619; 356/436, 134, 136; 250/577; 73/53, 61 R, 19.01, 19.03, 861.04, 861.41

[56] References Cited

U.S. PATENT DOCUMENTS

| | | | |
|---|---|---|---|
| 3,059,443 | 10/1962 | Garner | 62/129 X |
| 3,485,262 | 12/1969 | Perren | 137/386 |
| 3,636,360 | 1/1972 | Oishi et al. | 250/218 |
| 3,895,235 | 7/1975 | Melone | 250/577 |
| 4,064,826 | 12/1977 | Pauli | 116/117 C |
| 4,134,022 | 1/1979 | Jacobsen | 340/619 X |
| 4,155,013 | 5/1979 | Spiteri | 250/577 |
| 4,246,489 | 1/1981 | Yoshida et al. | 250/577 |
| 4,316,364 | 2/1982 | Spauschus | 62/129 |
| 4,328,682 | 5/1982 | Vana | 62/196 B |
| 4,354,180 | 10/1982 | Harding | 340/619 |
| 4,559,454 | 12/1985 | Kramer | 250/577 |
| 4,644,755 | 2/1987 | Esslinger et al. | 62/126 |
| 4,788,444 | 11/1988 | Williams | 340/619 X |
| 4,859,864 | 8/1989 | Smith | 250/577 |

Primary Examiner—Harry B. Tanner
Attorney, Agent, or Firm—Daniel Kramer

[57] ABSTRACT

A bubble detector for a liquid stream flowing within a conduit comprising a walled chamber communicating with the conduit interior, the chamber being positioned to trap and accumulate bubbles entrained with the liquid stream. A window in the chamber wall for optically examining the chamber, the window having its inner surface positioned to provide an interface with the chamber contents. Means for distinguishing between liquid and gas in the chamber comprising a light source positioned to direct its light toward the window inner surface, and a light sensor oriented to receive light reflected from the window inner surface the light source being positioned at such angle to the window inner surface that transmission of light with refraction occurs when liquid is present in the chamber and total internal reflection occurs when gas is present in the chamber. And an output device responding to the sensor for taking an action when a predetermined volume of bubbles have accumulated in the chamber.

12 Claims, 3 Drawing Sheets

APPARATUS FOR DETECTING SMALL BUBBLES IN A PRESSURIZED FLUID STREAM

FIELD OF THE INVENTION

The present invention relates to bubble detectors which function with respect to a liquid stream flowing within a conduit. The invention further relates to detectors utilizing optics for detecting the presence of bubbles. The invention further relates to such optical sensors positioned within a conduit which includes a chamber for trapping and accumulating small bubbles.

BACKGROUND OF THE INVENTION

Refrigeration systems are employed to produce cooling of a product or an environment. To do this cooling they abstract heat from that product or environment at a lower temperature level and reject the abstracted heat at a higher temperature level along with the heat equivalent of the thermal or mechanical energy utilized to move the abstracted heat from the lower to the higher temperature level. Though there are many types of refrigeration systems, the most common type uses a volatile refrigerating fluid, or refrigerant, circulated in a sealed system. The sealed system includes the following components:

A first heat transfer element or evaporator for boiling liquid refrigerant to a vapor thereby cooling the product or environment adjacent the evaporator, A compressor, conduit connected to the evaporator to draw vapor from it, thereby lowering the pressure in the evaporator. The compressor discharges the compressed vapor at an elevated pressure to a second heat transfer element or condenser which rejects heat from the compressed vapor to an air or water ambient, thereby condensing the compressed vapor to a liquid. The liquid refrigerant is returned to the evaporator by a conduit known as a liquid line to repeat the cooling effect. Before the liquid enters the evaporator it passes through a restrictor which may be in the form of an automatic control valve usually known as an expansion valve. When the expansion valve is designed to respond to temperatures at the vapor outlet, also called suction outlet, of the evaporator, it is called a thermal expansion valve or TXV; In small systems the restrictor is not adjustable and is in the form of a tube with a tiny bore known also known as a capillary tube or cap tube. The restrictor, whatever its type, lowers the pressure of the liquid refrigerant from the higher pressure found in the condenser to the lower pressure found in the evaporator and also regulates the flow of the liquid refrigerant into the evaporator to exactly that amount which the evaporator can evaporate.

In larger systems a holding tank called a liquid receiver or receiver is positioned in the liquid line between the condenser and the expansion valve. The receiver may be installed in a branch in the liquid line so that the flow from the condenser to the expansion valve bypasses the receiver, or in an alternate construction the receiver may be installed so that the full flow from the condenser to the expansion valve traverses the receiver.

The correct operation of refrigeration system requires that liquid flowing to the expansion valve (TXV) be substantially bubble free. Bubbles in the liquid stream flowing to the TXV severely degrade its operation and the operation, capacity and reliability of the whole system. In order to enable an operator or service person to observe whether there are bubbles in the liquid flowing to the TXV there is generally provided a device called a liquid sight glass positioned in the liquid line before the TXV. The liquid sight glass is a fitting generally designed to accommodate the full liquid flow to the TXV. The fitting has a transparent window allowing the operator to see the condition of the liquid flowing. If there is a receiver in the liquid line, the sight glass is positioned in the liquid line between the receiver and the TXV.

The presence of bubbles in the liquid stream flowing to the TXV generally is an indication of some system problem. Depending on the size and persistence of the bubbles the problem may be minor, not requiring any action, or serious requiring immediate action.

Vapor bubbles can exist in the flowing liquid refrigerant for short periods of time without causing excessive cooling capacity loss. However, a continuous stream of vapor bubbles mixed with the flowing liquid can seriously degrade system capacity thereby allowing the cooled product or environment to become warm. The consequences of degraded system capacity depend on the product or environment cooled. For example: if food, spoilage; if human, discomfort, dissatisfaction and loss of production; if computers, catastrophic loss of data and shut-down.

Further, if the refrigerant is a halogen type known as a CFC or HCFC, the loss to the atmosphere could contribute to serious environmental problems including loss of stratospheric ozone and increasing the earth temperature via the so-called greenhouse effect.

Persistent bubbles in the refrigeration system liquid line first suggest one of the following conditions:
(1) Low refrigerant level in the system receiver. This is an alarm situation indicative of a leak in the refrigeration piping system and a loss of refrigerant.
(2) Insufficient condensing pressure. The pressure of the flowing liquid refrigerant is at a saturation temperature which is below the ambient temperature surrounding the piping. This causes a boiling of the liquid refrigerant. This situation can require either a control action or an alarm or both.
(3) Excessive pressure drop in liquid pressure caused by a rise in liquid line elevation or a restriction in receiver or liquid line or a plugged filter-drier.

A Bubble detector of the present invention positioned at one or more points within the liquid flow stream can be employed to distinguish between a bubbling and an bubble-free condition of the liquid flow stream and to provide an alarm or to take some corrective measure.

There are other applications in refrigeration for a bubble detector besides the liquid line application described in the preceding paragraphs.

For example, a bubble detector can be used to determine the end of defrost for reverse flow hot gas defrost. This type of defrost is common on multi-compressor supermarket refrigeration systems. The bubble detector would be used to monitor the condensed defrost gas flowing from the evaporator and returning to the liquid line and to terminate the defrost when bubbles appear.

A bubble detector could also be positioned in the liquid line between the condenser and the receiver to monitor the liquid flow stream entering the receiver.

That flow stream normally is not pure bubble-free liquid but has liquid which includes many bubbles. In the abnormal case, where the refrigeration system is overcharged, that flow stream becomes bubble-free. A bubble detector position in the liquid line at the receiver inlet, therefore could be employed to diagnose a condition of system overcharge.

In the systems where there is filter drier installed in the liquid line two bubble detectors would be installed in the liquid line, one immediately before the filter drier, the inlet detector, the second, immediately after the filter drier, the outlet detector.

The condition of bubbles at the outlet detector coincident with a condition of no bubbles at the inlet detector would trigger an alarm condition warning of a plugged filter drier or a drier having excessive pressure drop for the subcooling available.

The bubble detector of the present invention utilizes the optical principle of refraction and the optical principle of total internal reflection to distinguish between the presence of liquid and vapor at an optical interface at which a light beams is directed.

Bubble detectors which utilize the principles of total internal reflection and which depend on refractive differences between a liquid and a gas of a monitored fluid stream are taught in Kramer's U.S. Pat. No. 4,559,454 and in Smith's U.S. Pat. No. 4,859,864.

The transition between refraction and total internal reflection relies on differences in refractive index between the liquid phase and the vapor phase of the monitored fluid and on the angle of light from a source impinging on an interface between a transparent window having a refractive index and the monitored fluid, whereby a condition of total internal reflection exists when vapor only occupies the interface, and partial reflection and partial transmission with refraction when liquid only occupies the same interface. The condition of total internal reflection arises when light moves from a first transparent medium with a first index of refraction through an interface at an angle to a perpendicular to the interface erected in the first medium, to a second transparent medium with a second index of refraction and the angle to the perpendicular is greater than a critical angle. The angle is expressed by an equation to be defined later.

Under conditions of total internal reflection the internal surface of the optical window at the interface between the window and the monitored fluid acts like a high efficiency silver mirror. In order to employ the transition between total internal reflection and refraction for the purpose of sensing the difference between liquid and vapor refrigerant, the optical construction must be such that the angle of incident light rays striking the interface between the window and the monitored fluid must be greater than the critical angle of incidence for vapor and less than the critical angle of incidence for the liquid refrigerant.

The critical angle of incidence is the angle between a perpendicular erected to the interface between the glass and the refrigerant, and a ray of light moving within the glass toward the refrigerant-glass interface. The critical angle is the special case where the ray of light, having left the glass, has a path in the refrigerant which is parallel with the surface of the glass. Light moving within the glass toward the interface with the refrigerant at an angle greater than the critical angle is totally reflected back into the glass. Hence, the critical angle is also known as the angle for total internal reflection. The critical angle is calculated using Snell's law (Willebrord Snell 1621) from the formula $$\text{Sin Critical Angle} = \frac{\text{Index Medium}}{\text{Index Glass}}$$

The table shown below lists the index of refraction and the critical angle of incidence for various liquid and gaseous refrigerants, relative to a typical glass having an index of Refraction of 1.517.

TABLE 1

| Medium | Index | Critical Angle Of Incidence (Degrees) |
|---|---|---|
| Gas | 1.000 | 41.2 (for refrigerants vapors, air and vacuum) |
| Liquid | | |
| R11 | 1.362 | 63.9 |
| R12 | 1.288 | 58.1 |
| R22 | 1.234 | 54.4 |
| R113 | 1.357 | 63.5 |
| R114 | 1.294 | 58.5 |
| R502 | 1.234 | 54.4 |
| R717 | 1.325 | 60.9 |

Materials other than glass with similar optical properties could be used as well.

Examination of the table shows that for the liquid refrigerants the smallest critical angle is 54.4° while for all the gases the critical angle is 41.2°. The present invention teaches an apparatus and method which employs the principle of total internal reflection together with a bubble accumulating chamber positioned in a flow stream of liquid refrigerant to monitor the flow stream and to initiate action when the accumulation of bubbles reaches a significant level.

SUMMARY OF THE INVENTION

The present invention is directed towards an apparatus for detecting vapor or gas bubbles in a liquid stream flowing within a conduit. The apparatus comprises a conduit, and chamber means communicating with the conduit and positioned above it for containing liquid conveyed by the conduit and for receiving and accumulating bubbles conveyed to it by the liquid stream flowing within the conduit. By this means, liquid, initially within the chamber is displaced by the accumulated vapor bubbles. The chamber means includes a wall for containing and preventing loss to the atmosphere of its liquid and vapor or gas contents.

Window means are provided in the wall for permitting light to enter and leave the chamber. The window means has a reference axis and an interior surface subject to the liquid or vapor contents of the chamber. The window means also has an exterior surface. There is an imaginary line erected in the window means from a point on its interior surface perpendicular to that surface. A light means is provided which is positioned adjacent the exterior surface of the window means in a first position for directing the light beam emanating from the light means in a path which intersects the point at an angle with the perpendicular. The angle is selected to produce a condition of transmission with refraction on the presence of liquid in the chamber and a condition of total internal reflection on the presence of vapor in the chamber. There is a light sensor positioned adjacent the exterior surface of the window means in a second position for receiving light emanating from the light source and reflected from the point.

BRIEF DESCRIPTION OF THE DRAWINGS

The foregoing summary as well as the following description of preferred embodiments of the invention, will be better understood when read in conjunction with the appended drawings. For the purpose of illustrating the invention there are shown in the drawings embodiments which are presently preferred, it being understood, however, that the invention is not limited to the specific instrumentalities or the precise arrangement of elements disclosed.

DETAILED DESCRIPTION OF THE INVENTION

Figure 1:
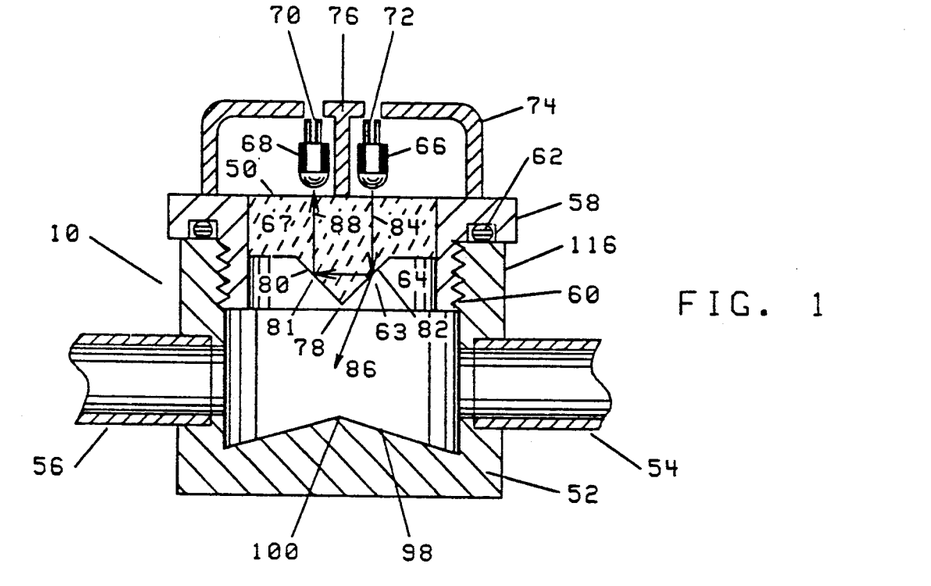
FIG. 1 is a side elevation in cross section of an enlarged view of an embodiment of the bubble sensor of the present invention.

Referring now to the drawings, wherein like references are used to indicate like elements, there is shown in FIG. 1 a side elevation in cross section of a first embodiment of the bubble detector 10 of the present invention. Conduit portion 52 of the detector has a liquid inlet connection 54 having an inside diameter and a liquid outlet connection 56. Solder connections are shown, though other types of connections are suitable. These connections are employed for conveying through the body of the detector the liquid stream which is to be subjected to the scrutiny of the detector. Examples of applications involving such liquid streams are described in connection with FIGS. 8 and 9. The conduit portion is of brass although other materials including aluminum, steel or polymeric materials having the necessary chemical pressure and temperature capabilities are suitable. Steel and aluminum are suitable materials for use with ammonia refrigerant. Any of the above named materials are suitable for use with fluorocarbon or chlorofluorocarbon refrigerants. Wall 116 of the conduit portion 52 has internal threads 60 into which the window assembly 58 is screwed. O-ring gasket 62 is provided to prevent leakage of refrigerant from the joint between the window assembly 58 and the conduit portion 52. The method of attachment of the window 67 to the conduit portion 52 is not germane to the present invention and other methods of attachment including permanent attachment as by soldering or epoxying the window 67 directly to the conduit portion are equivalent.

Wall 116 is constructed sufficiently high to provide a chamber 64, positioned over the conduits 54,56, into which small vapor bubbles will rise and accumulate, thereby forming a large bubble of vapor which will, when present, change the path 84/88 of the light beam emitted by LED 66.

The window 67, positioned in window assembly 58, is formed by molding glass having an index of refraction of 1.517. The window can be made also by grinding and polishing. Other window materials having similar index of refractions are suitable. The window material need not be transparent. Translucent materials such as polytetrafluoroethylene (DuPont tradename Teflon) and Nylon have proved satisfactory in tests. Molded Nylon brand polyimide construction allows more flexibility in design, simplifies sealing against leakage and provides the possibility of low cost construction for mass markets. Teflon brand tetrafluoroethylene or other similar polymers would be preferred materials where the window must be subjected top great physical or thermal shock as in space or nuclear applications, or where the fluid to be examined is likely to be highly corrosive. Window 67 is formed with a planar exterior surface 50 and a prismatic interior surface having prism faces 80 and 82 which intersect in prism edge 78. A light emitting diode (LED) 66 (Motorola MLED930) is positioned immediately adjacent the exterior surface 50 of window 67 to direct its beam in a path which intersects prism face 82 at a point. Other light sources such as incandescent or gas discharge work satisfactorily though light sources having a long service life are preferred.

Sensor 68 is a photosensitive transistor. Motorola MRD360 is preferred, although other photosensitive devices will work satisfactorily. Sensor 68 is positioned to receive the light which has been twice subject to total internal reflection at surfaces 80,82 of prismatic window 67.

Through window 67 is shown installed in the wall of chamber 64 in a substantially horizontal plane, the plane of the window 67 can be either horizontal or at an angle with the horizontal, so long as the lowest point 63 of anticipated total internal reflection is a sufficient height above the liquid inlet connection 54. In one embodiment the point 63 is elevated above connection 54 by a distance equal to 0.75 times the inside diameter of connection 54.

The bubble detector is constructed to inhibit the reflection to light sensor 68 of light refracted via path 86 into the detector interior. In one embodiment, prism face 80 is covered with a reflective coating 81 of aluminum. In other embodiments platinum, gold or any other opaque reflective light colored bondable material are employed to fully or partially cover prism face 80. The reflective coating provides a reflective surface for light being reflected from prism face 82 when accumulated bubbles exist at that face and at the same time, blocks light being reflected from the interior surfaces of detector 10 when liquid exists at prism face 82.

In an alternative embodiment surface 98 of conduit portion 52 is formed in the shape of a cone having its central axis collinear with the axis of window 67 for the purpose of reflecting incident light away from window 67 thereby inhibiting the return to sensor 68 of light refracted via path 86 into the detector interior. In another alternate embodiment a light absorbing coating is provided on the interior of the conduit portion 52 of detector 10 to inhibit unwanted return of incident light to sensor 68.

Protective hood 74 provides mechanical protection and support for the LED 66 and the sensor 68 and restricts the entry of ambient light. Interior wall 76 prevents light rays from light emitting diode 66 from directly reaching sensor 68.

Figure 2:
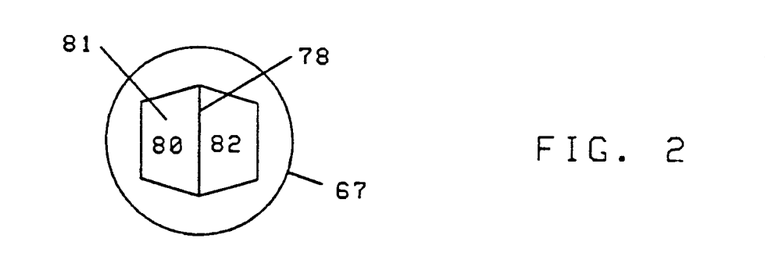
FIG. 2 is a plan view of the under side of a prismatic window employed in one embodiment of the present invention.

FIG. 2 is a view of window 67 from its underside, that is from a position within chamber 64. The prism faces 80 and 82 are visible along with their line of intersection 78. In alternate embodiments the prism is conical, rectangular or pyramidal.

Referring again to FIG. 1, when bubbles became entrained in the liquid stream entering the bubble detector 10, liquid is displaced from chamber 64 and replaced by a bubble of vapor. The path 84 of light emitted by LED 66 is then governed by the law of total internal reflection at the prism face 80 now covered partially by the vapor bubble, and the intensity of light reaching sensor 66 increases. This increase in light intensity is enough to change the voltage across of the photosensitive element of sensor 66 and cause a significant change in the output voltage of a detector circuit. Such a detector circuit is described in connection with FIG. 7.

Figure 3:
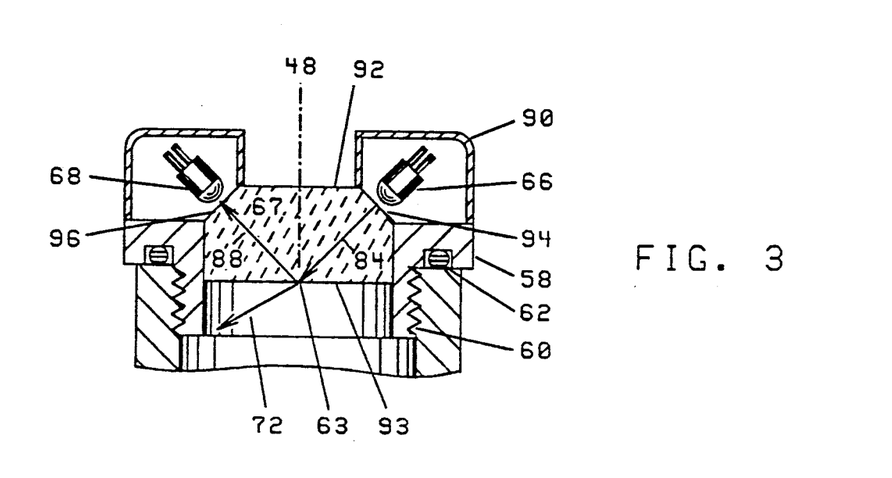
FIG. 3 is side elevation in cross section of the window of another embodiment of the present invention having a flat interior surface.

FIG. 3 is a side elevation in cross section of the upper or chamber portion of another embodiment of the present invention in which window 67 is formed with a planar interior surface 93. Window 67 has an exterior surface having a planar face 92 which is substantially parallel to the interior planar face 93. In addition, the exterior surface of window 67 has two planar facets 94 and 96. In an alternate embodiment, facets 94 and 96 are part of the frustrum of a conical shape. Facet 94 provides a light input face for LED 66. Facet 96 provides a light output face for sensor 68. The light emitted by LED 66 enters window 67 in path 84 and intersects interior planar surface 93 at point 63. An imaginary perpendicular 48 to interior face 93 is erected at point 63 and the angle of entering light path 84 is measured from perpendicular 48. Perpendicular 48 also constitutes a reference axis for window 67. On a condition of liquid present in chamber 64 the light following path 84 will be transmitted into the liquid residing in chamber 64 with refraction via path 72. When the liquid adjacent point 63 is displaced by a vapor bubble, the light from LED 66 following path 84 will subject to total internal reflection and substantially all the light entering window 67 from LED 66 will reach sensor 68 via path 88, thereby actuating an alarm or initiating some other action. A hood 90 provides mechanical support for the LED and the sensor, provides light isolation, and enables a user to observe the condition of the fluid within chamber 64 through the central hole in hood 90 at the same time the LED 66 and sensor 68 are automatically monitoring the condition of the fluid within the chamber 64.

Figure 4:
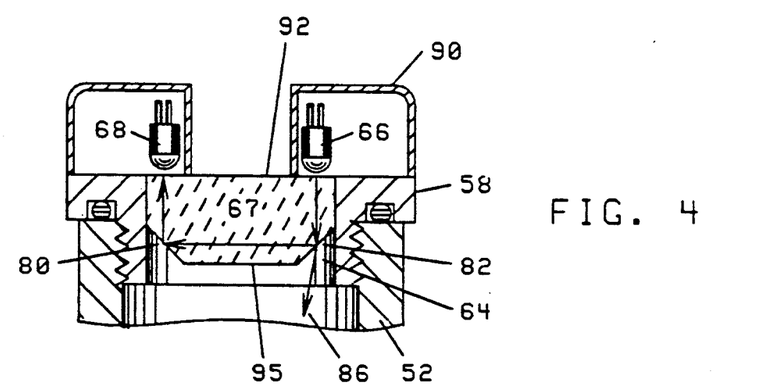
FIG. 4 is a another embodiment of the present invention illustrating a prismatic window having a flat central portion.

In FIG. 4 window 67 has a planar exterior face 92 and a prismatic interior surface having two prism faces, 82 and 80 which are separated by a planar portion 95. Planar portion 95 is substantially parallel to exterior window surface 92. The light from LED 66 is directed in a path 84 which is parallel to the window axis and is positioned to intersect prism face 82. On reflection from prism face 82 the light traverses window 67 and is reflected back to sensor 68 by prism face 80.

Figure 5:
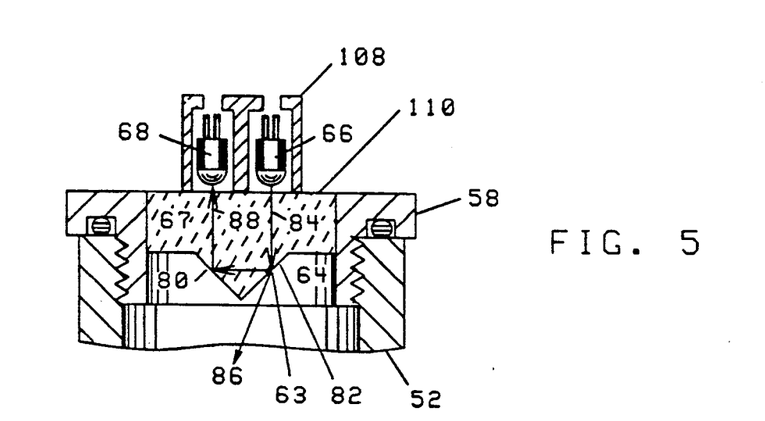
FIG. 5 shows another embodiment of the present invention showing a prismatic window having a centrally positioned axial hood.

The embodiment of the present invention shown in FIG. 5 is similar to that of FIG. 1 with the exception that there is provided a centrally positioned axial protective hood 108 for protecting and supporting the LED 66 and sensor 68, thereby providing an annular surface portion 110 of the exterior surface of window 67 through which an observer can monitor the condition of the fluid within chamber 64 while the mechanism of the invention automatically monitors the condition of the same fluid.

Figure 6:
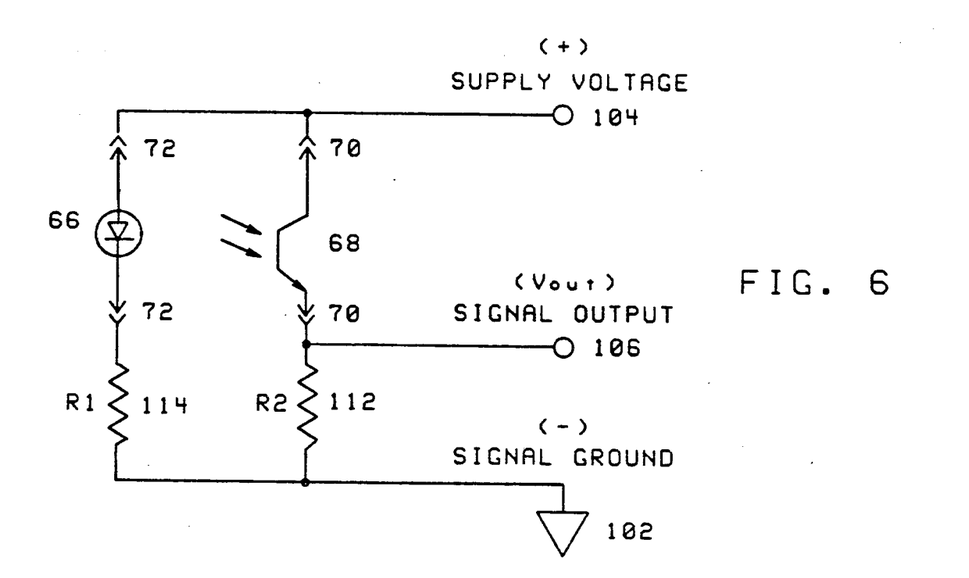
FIG. 6 is a schematic diagram for the wiring of the light source, the sensor and the output circuit with which the bubble detector of the present invention can be used.

FIG. 6 is a schematic wiring diagram of a simple light input and control output circuit which is applicable to any of the embodiments of the present invention described herein. In FIG. 6 the DC potential difference between terminal 104 and ground 102 is 12 volts. R1 and R2, resistors 114 and 112, are both 2200 ohms. The output voltage between terminal 106 and ground 102 is 10.9 volts with liquid in chamber 64 in contact with prism faces 82,84 and 1.6 volts with a vapor bubble in contact with the prism faces. On a change from the higher to the lower voltage, a relay, not shown, closes a circuit to sound an alarm. In other embodiments of the present invention the change from higher to lower voltage effectuates an increase in condensing pressure in the system of FIGS. 8 or 9 by stopping or cycling condensor fan 40 or by flooding the tubes of condenser 24 by means well known to those versed in the refrigeration arts. Many other circuits capable of achieving similar results are known to those skilled in these electronic arts. In an alternate embodiment of the present invention, an alternating current power supply having a 400 Hz frequency supplies the power for the LED and an AC amplifier peaking at 400 Hz and having the sensor 68 as input provides output for the sensor 68 which is free from false sensor responses caused by changes in the ambient light inadvertently reaching sensor 68.

Figure 7:
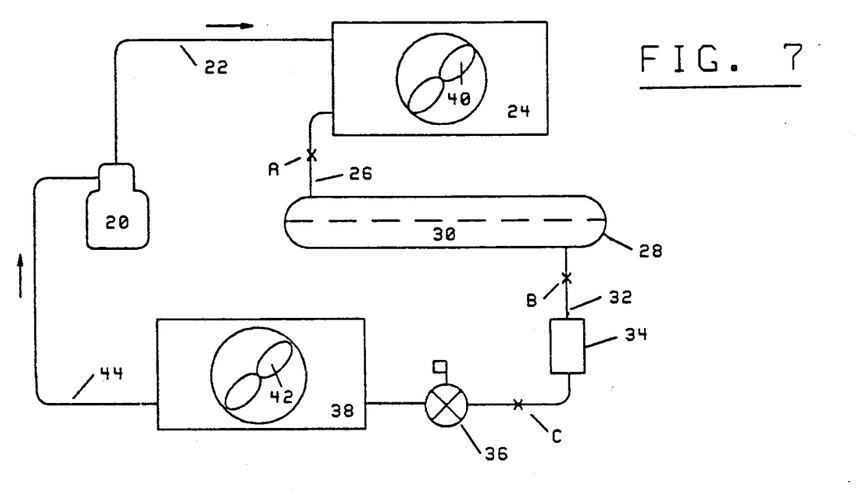
FIG. 7 is a schematic piping diagram of one type of refrigeration system with which the bubble sensor of the present invention can be used.

FIG. 7 is a schematic piping diagram with which the bubble sensor is used. Compressor 20 draws refrigerant vapor from evaporator 38 via suction line 44 and discharges it, compressed to a higher pressure, to condenser 24 via discharge line 22. Condenser 24 employs motor driven fan 40 to draw ambient air over the condenser surface, cooling and condensing the refrigerant flowing therein to a liquid. The liquid is conveyed by conduit 26 to receiver 28 in which a pool of liquid refrigerant 30 resides until required by the refrigerating system. Liquid line 32 conveys liquid refrigerant from pool 30 in receiver 28 to evaporator 38 by way of drier 34 and pressure reducing expansion valve 36. Evaporator 38 transmits the cooling effect of the evaporating refrigerant to the environment by way of motor driven evaporator fan 42.

Locations A, B and C are positions where any of the bubble detectors previously described can be installed for the following alarm, diagnostic or remedial purposes.

A bubble sensor installed at B functions to indicate the presence or absence of a sufficient quantity of refrigerant 30 in receiver 28. So long as there is a sufficient quantity of liquid refrigerant 30 present in receiver 28 the flow stream of liquid refrigerant past point B and a bubble sensor installed there will be bubble free. As soon the liquid level drops near the bottom of receiver 28 then vapor will be entrained along with liquid refrigerant entering the liquid line 32 and the bubble detector at point B will provide an alarm or will initiate corrective action as provided by the system designer. One such corrective action comprises raising the system condensing pressure by stopping or cycling condenser fan 40. Intermittent or continuous bubbles at point B can have other causes many of which are described in the Background section of this specification.

In another embodiment of the invention one bubble detector of the present invention is installed at position B and a second bubble detector is installed at position C. A satisfactory 'no-alarm' condition occurs when both the bubble detectors at B and C indicator no bubbles. When both indicate bubbles a shortage of charge is most likely. When the bubble detector at B indicates a 'no-bubble' condition and the bubble detector at C indicates a 'bubbles present' condition the inference to be drawn is that the drier 34 is plugged or that there is insufficient subcooling in the liquid refrigerant for it to resist flashing when subjected to the pressure drop imposed by tranverse of the liquid through the liquid line drier 34.

A bubble detector located at position A in FIG. 7 provides an indication of overcharge. Under conditions of correct charge where the level of liquid refrigerant 30 within receiver 28 is higher than the bubbling level and also lower than the filled level there will be a substantially continuous flow of vapor along with liquid flowing to the receiver 28. As the receiver fills, the proportion of bubbles accompanying the liquid refrigerant gradually decreases, and the proportion of bubbles decreases to zero when the receiver is completely filled thereby causing the bubble detector to issue a warning of overcharge.

Figure 8:
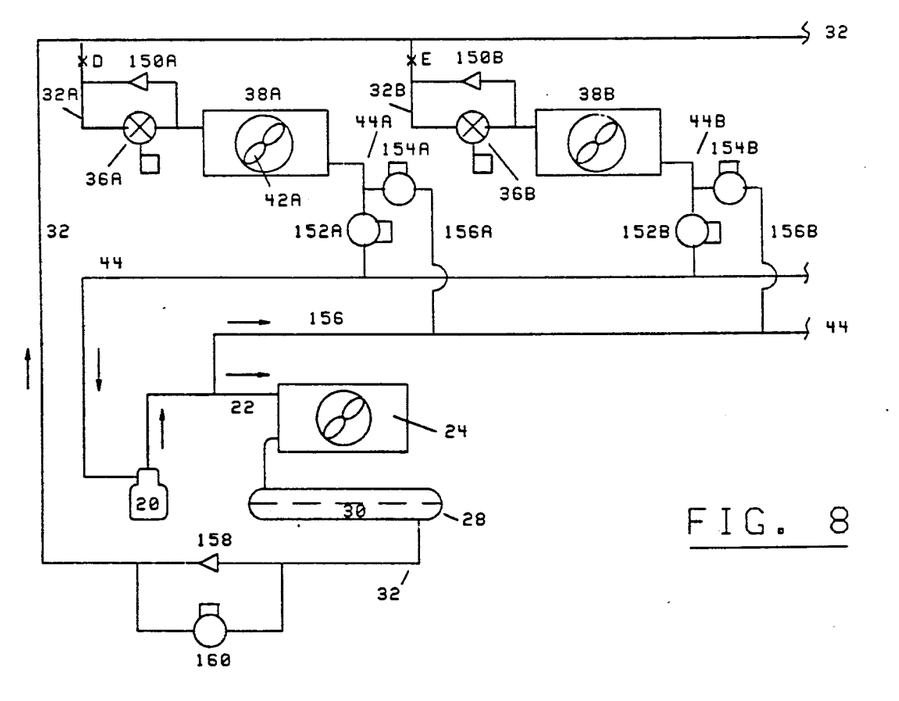
FIG. 8 is a schematic piping diagram of a refrigeration system employing hot gas defrost in which the bubble sensor of the present invention is used as a defrost terminator.

FIG. 8 is a schematic piping diagram of a refrigeration system having multiple evaporators two of which are piped for hot gas defrost in an arrangement called reverse cycle hot gas defrost also known as a regenerative defrost. In FIG. 8 during refrigeration, compressor 20 draws vapor from suction line 44 and discharges it at higher pressure to the condenser 24 via discharge line 22. Condensed refrigerant liquid flows to receiver 28 and is stored there in pool 30 until required by system operation. Liquid from pool 30 is delivered from the receiver 28 to evaporators 38A, 38B and other evaporators not shown via main liquid line 32. Positioned within main liquid line 32 is a spring loaded check valve 158 designed to product a pressure drop in the liquid flow stream of about 15 psi. Bypassing check valve 158 is solenoid valve 160 which is designed to allow full liquid flow with minimum pressure drop, typically 2 psi. Solenoid valve 160 is open during refrigeration.

Each evaporator is supplied liquid refrigerant from the main liquid line 32 via branch liquid lines 32A and 32B each having expansion valves 36A and 36B respectively to reduce the pressure of and control the flow of refrigerant to their respective evaporators. Each expansion valve is bypassed by a check valve 150A and 150B respectively which is positioned to allow flow from the evaporator into the liquid line and to stop flow from the liquid line into the evaporator, thereby ensuring that liquid flow from the liquid line to the evaporator occurs only through the expansion valves 36A and 36B. Vapor from each evaporator is delivered to main suction line 44 by branch suction lines 44A and 44B respectively. Each branch suction line has a suction solenoid 152A and 152B installed to allow and prevent flow. Suction solenoids 152A and 152B are open during refrigeration.

A hot gas defrost main 156 is tapped off discharge line 22. Branches 156A and 156B from hot gas main 156 supply hot gas into suction branches 44A and 44B under control of hot gas solenoid valves 154A and 154B for defrost of evaporators 38A and 38B respectively.

Only one evaporator at a time is defrosted. Timers or other types of defrost controls arrange the defrost sequence. The control sequence during the defrost of evaporator 38A is as follows: Evaporator fan 42A stops. Suction solenoid 152A closes. Hot gas solenoid 154A opens. Liquid solenoid 160 closes, thereby introducing a 15-20 psi pressure drop in liquid line 32. Since the pressure in liquid line 32, even with the 20 psi drop introduced by valve 158, is still many psi higher than the pressure in defrosting evaporator 38A, the liquid, resulting from the introduction of and condensation of hot gas in defrosting evaporator 38A, remains in the evaporator. As the pressure in the defrosting evaporator 38A rises, liquid refrigerant gradually begins to be expelled from the evaporator into liquid line 32 via check valve 150A. A bubble detector of the present invention is positioned in the branch liquid line at D. So long as there is still bubble free liquid being expelled from defrosting evaporator 38A the evaporator is not completely defrosted. As soon as vapor along with liquid is expelled from the defrosting evaporator the defrost is complete. The bubble detector will terminate defrost of evaporator 38A at that time by shutting hot gas solenoid 154A, opening liquid solenoid 160 and suction solenoid 152A and starting the evaporator fans 42A.

From the foregoing description, it can be seen that the present invention comprises an improved bubble detector having applications within and outside the refrigeration area. It will be appreciated by those skilled in the art that changes could be made to the embodiments described in the foregoing description without departing from the broad inventive concept thereof. It is understood, therefore, that this invention is not limited to the particular embodiment or embodiments disclosed, but is intended to cover all modifications which are within the scope and spirit of the invention as defined by the appended claims.

I claim:

1. Apparatus for detecting gas bubbles in a liquid stream flowing within a conduit comprising
   inlet connection means for connecting to the conduit,
   chamber means communicating with the inlet connection means and positioned above it for containing liquid and for receiving and accumulating gas bubbles conveyed to it by the liquid stream whereby the liquid is displaced by the accumulated gas bubbles, the chamber means including a wall for containing and preventing escape to the atmosphere of its liquid and gas contents,
   window means positioned in the wall for permitting light to enter and leave the chamber means, an exterior surface, and an interior surface subject to the liquid or gas contents of the chamber means,
   a point on the interior surface positioned at a height above the inlet connection means,
   an imaginary line erected in the window means, the line being perpendicular to the interior surface at the point,
   light source means positioned adjacent the exterior surface of the window means in a first position for directing a light beam in a path which intersects the point at an angle with the perpendicular line, the angle being selected to produce a condition of transmission with refraction on the presence of liquid in the chamber means, and a condition of total internal reflection on the presence of gas in the chamber means and
   light sensor means positioned adjacent the exterior surface of the window means in a second position for receiving light emanated from the light source means and reflected from the point, and further including means activated by the light sensor for performing a first function on the presence of liquid adjacent the window interior surface and for performing a second function on the presence of gas adjacent the window interior surface, and further including a refrigerating system having multiple evaporators and a reverse cycle hot gas defrost system for defrosting at least one evaporator, said hot gas defrosting evaporator having a suction outlet and having also a liquid inlet with a conduit connected thereto and the bubble detecting apparatus connected therein, a conduit for providing hot gas to the suction outlet during defrost and further providing that the second function is the termination of the defrost.

2. Apparatus as recited in claim 1 where the material of the window means is translucent polyimide.

3. Apparatus for detecting gas bubbles in a liquid stream flowing within a horizontal conduit comprising inlet connection means for connecting to the conduit, chamber means communicating with the inlet connection means and positioned above it for containing liquid and for receiving and accumulating gas bubbles conveyed to it by the liquid stream whereby the liquid is displaced by the accumulated gas bubbles, the chamber means including a wall for containing and preventing escape to the atmosphere of its liquid and gas contents, window means having a vertical axis, said window means being positioned in the wall at the top of the chamber means for permitting light to enter and leave the chamber means, an exterior surface, and an interior surface subject to the liquid or gas contents of the chamber means, a point on the interior surface positioned at a height above the inlet connection means, an imaginary line erected in the window means, the line being perpendicular to the interior surface at the point, light source means positioned adjacent the exterior surface of the window means in a first position for directing a light beam in a downward path which intersects the point at an angle with the perpendicular line, the angle being selected to produce a condition of transmission with refraction on the presence of liquid in the chamber means, and a condition of total internal reflection on the presence of gas in the chamber means and light sensor means positioned adjacent the exterior surface of the window means in a second position for receiving light emanated from the light source means and reflected from the point.

4. Apparatus for detecting gas bubbles in a liquid stream flowing within a horizontal conduit comprising inlet connection means for connecting to the conduit, chamber means communicating with the inlet connection means and positioned above it for containing liquid and for receiving and accumulating gas bubbles conveyed to it by the liquid stream whereby the liquid is displaced by the accumulated gas bubbles, the chamber means including a wall for containing and preventing escape to the atmosphere of its liquid and gas contents, window means having a vertical axis, said window means being positioned in the wall at the top of the chamber means for permitting light to enter and leave the chamber means, an exterior surface, and an interior surface subject to the liquid or gas contents of the chamber means, a point on the interior surface positioned at a height above the inlet connection means, an imaginary line erected in the window means, the line being perpendicular to the interior surface at the point, light source means positioned adjacent the exterior surface of the window means in a first position for directing a light beam in a downward path which intersects the point at an angle with the perpendicular line, the angle being selected to produce a condition of transmission with refraction on the presence of liquid in the chamber means, and a condition of total internal reflection on the presence of gas in the chamber means and light sensor means positioned adjacent the exterior surface of the window means in a second position for receiving light emanated from the light source means and reflected from the point, further providing that said window means is fabricated of a translucent material.

5. Bubble detecting means as recited in claim 4 where the translucent window means material is polymide.

6. Apparatus for detecting gas bubbles in a liquid stream flowing within a horizontal conduit comprising inlet connection means for connecting to the conduit, chamber means communicating with the inlet connection means and positioned above it for containing liquid and for receiving and accumulating gas bubbles conveyed to it by the liquid stream whereby the liquid is displaced by the accumulated gas bubbles, the chamber means including a wall, having an interior surface, for containing and preventing escape to the atmosphere of its liquid and gas contents, window means having a vertical axis, said window means being positioned in the wall at the top of the chamber means for permitting light to enter and leave the chamber means, an exterior surface, and an interior surface subject to the liquid or gas contents of the chamber means, a point on the interior surface positioned at a height above the inlet connection means, an imaginary line erected in the window means, the line being perpendicular to the interior surface at the point, light source means positioned adjacent the exterior surface of the window means in a first position for directing a light beam in a downward path which intersects the point at an angle with the perpendicular line, the angle being selected to produce a condition of transmission with refraction on the presence of liquid in the chamber means, and a condition of total internal reflection on the presence of gas in the chamber means and light sensor means positioned adjacent the exterior surface of the window means in a second position for receiving light emanated from the light source means and reflected from the point, and further providing means, contiguous only with the interior surface of the chamber wall, for preventing light having entered the chamber means from leaving the chamber means and impinging on the light sensing means.

7. Bubble detecting means as recited in claim 6 where the light preventing means comprises a light absorbing coating positioned only on the non-window interior surface of the chamber means.

8. Bubble detecting means as recited in claim 6 where the light preventing means comprises a conical shape formed in the interior surface of the wall of the chamber means, the shape having an axis and an apex, the shape being positioned coaxially with and opposite the window means, with its apex facing the interior surface of the window means, whereby light transmitted into the chamber means and striking the conical shape is deflected into the chamber means walls, thereby being prevented from leaving the chamber means and impinging on the light sensor means.

9. Apparatus for optically and visually detecting gas bubbles in a liquid stream flowing within a horizontal conduit comprising inlet connection means for connecting to the conduit, chamber means communicating with the inlet connection means and positioned above it for containing liquid and for receiving and accumulating gas bubbles conveyed to it by the liquid stream whereby the liquid is displaced by the accumulated gas bubbles, the chamber means including a wall for containing and preventing escape to the atmosphere of its liquid and gas contents, window means having a vertical axis said window means being positioned in the wall at the top of the chamber means for permitting light to enter and leave the chamber means, an exterior surface divided into a sensor part and a viewing part, and an interior surface subject to the liquid or gas contents of the chamber means, a point on the interior surface positioned at a height above the inlet connection means, an imaginary line erected in the window means, the line being perpendicular to the interior surface at the point, light source means positioned adjacent the sensor part of the exterior surface of the window means in a first position for directing a light beam in a downward path which intersects the point at an angle with the perpendicular line, the angle being selected to produce a condition of transmission with refraction on the presence of liquid in the chamber means, and a condition of total internal reflection on the presence of gas in the chamber means and light sensor means positioned adjacent the sensor part of the exterior surface of the window means in a second position for receiving light emanated from the light source means and reflected from the point, whereby a single apparatus, when installed in an conduit, provides both an electronic and a visual detection of bubbles in a liquid stream flowing within the conduit.

10. Bubble detecting apparatus as recited in claim 9 where the sensor part of the external surface is substantially centrally positioned on the external surface of the window means.

11. Bubble detecting apparatus as recited in claim 9 where the viewing part of the external surface is substantially centrally positioned on the external surface of the window means.

12. Bubble detecting apparatus as recited in claim 9 and further including hood means substantially enclosing the sensor part of the exterior surface, whereby the effect of external light on the sensors is minimized and the viewing part of the external surface of the window means is available for visual observation of the condition of the fluid flowing through the bubble detecting apparatus.

* * * * *